United States Patent
Vinayagamoorthy

(10) Patent No.: US 11,901,042 B2
(45) Date of Patent: Feb. 13, 2024

(54) ALGORITHM TO EVALUATE EFFICACY OF DETECTING CELLULAR VARIANTS IN A HETEROGENEOUS CELL POPULATION

(71) Applicant: Thuraiayah Vinayagamoorthy, Greensboro, NC (US)

(72) Inventor: Thuraiayah Vinayagamoorthy, Greensboro, NC (US)

( * ) Notice: Subject to any disclaimer, the term of this patent is extended or adjusted under 35 U.S.C. 154(b) by 1190 days.

(21) Appl. No.: 15/976,956

(22) Filed: May 11, 2018

(65) Prior Publication Data
US 2019/0348148 A1 Nov. 14, 2019

(51) Int. Cl.
| | | |
|---|---|---|
| *G16B 20/20* | (2019.01) | |
| *G16B 10/00* | (2019.01) | |
| *G16B 20/00* | (2019.01) | |
| *G16B 30/00* | (2019.01) | |
| *G16B 40/00* | (2019.01) | |
| *G16B 5/00* | (2019.01) | |
| *G16B 25/00* | (2019.01) | |
| *G16B 15/00* | (2019.01) | |
| *G16B 35/00* | (2019.01) | |
| *G16B 45/00* | (2019.01) | |
| *G16B 50/00* | (2019.01) | |
| *C12Q 1/6886* | (2018.01) | |

(52) U.S. Cl.
CPC ........... *G16B 20/20* (2019.02); *C12Q 1/6886* (2013.01); *G16B 5/00* (2019.02); *G16B 10/00* (2019.02); *G16B 15/00* (2019.02); *G16B 20/00* (2019.02); *G16B 25/00* (2019.02); *G16B 30/00* (2019.02); *G16B 35/00* (2019.02); *G16B 40/00* (2019.02); *G16B 45/00* (2019.02); *G16B 50/00* (2019.02); *C12Q 2600/154* (2013.01); *C12Q 2600/156* (2013.01)

(58) Field of Classification Search
None
See application file for complete search history.

(56) References Cited

PUBLICATIONS

Vinayagamoorthy. T. Simultaneous detection of multiple nucleic acid templates using modified primers. USA. U.S. Pat. No. 11,028,442 Jun. 8, 2021.

Talasaz. Systems and methods to detect rare mutations and copy number variation Feb. 8, 2022. U.S. Pat. No. 11,242,556.

Rixe Olivier, Bahassi El Mustapha. Methods for detection and quantification of EGFRvIII in the peripheral blood of GBM patients. Jan. 25, 2022. U.S. Pat. No. 11,230,738.

Eltoukhy; Helmy et al. Methods to determine tumor gene copy number by analysis of cell-free DNA. Feb. 8, 2022. U.S. Pat. No. 11,242,569.

*Primary Examiner* — Joseph Woitach

(57) ABSTRACT

Somatic mutations are associated with cancer progression and treatment using targeted therapies. Somatic mutations are not inherited and could be present at low concentrations in biopsy samples. Hence, there is a need for more sensitive assays to detect these changes in the presence of heterogeneous cell populations. The efficacy of such detection is determined by two factors; the ability to detect a minimum number of copies of the target mutation in the sample (Lower limit of detection), and the ratio of target mutation to that of wild-type in the sample (Tumor content). A new algorithm Detection Index (DI) is formulated to evaluate the efficacy of detection for a molecular testing method.

15 Claims, 2 Drawing Sheets

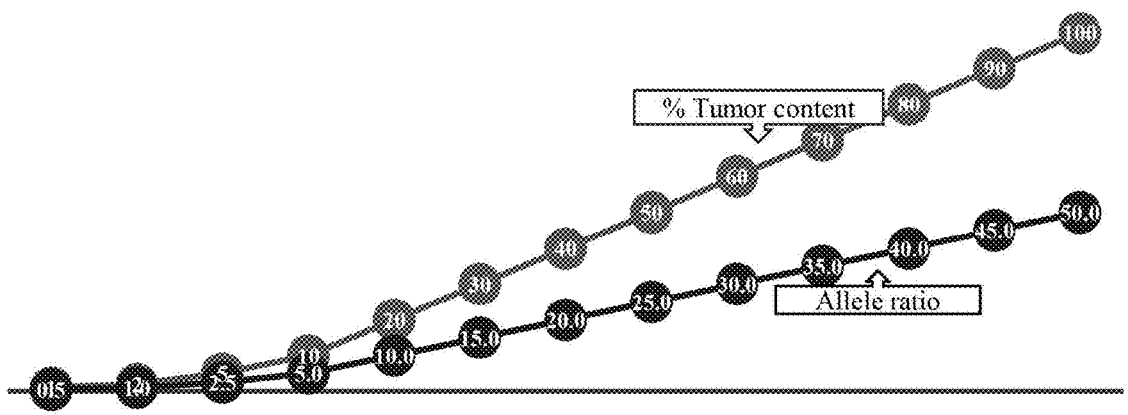
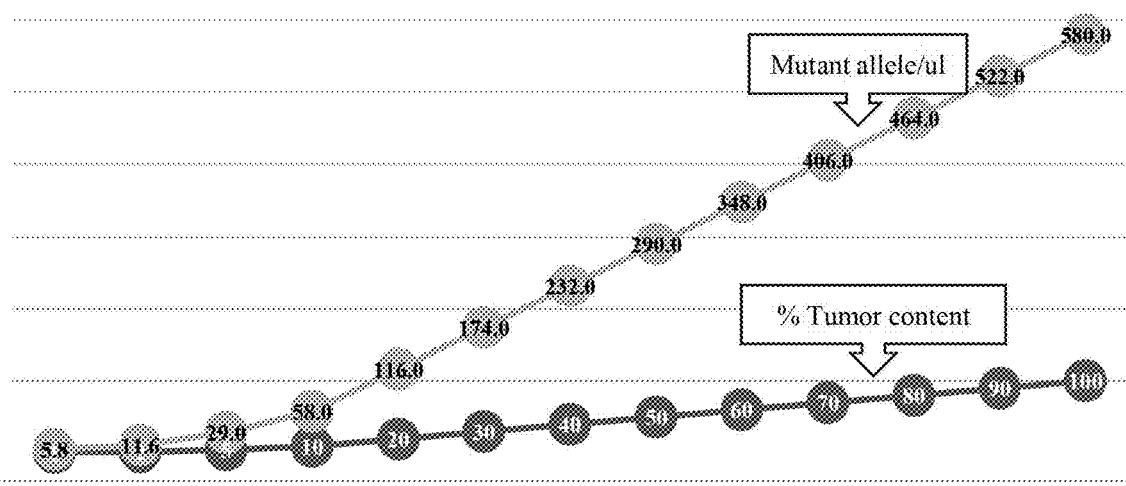

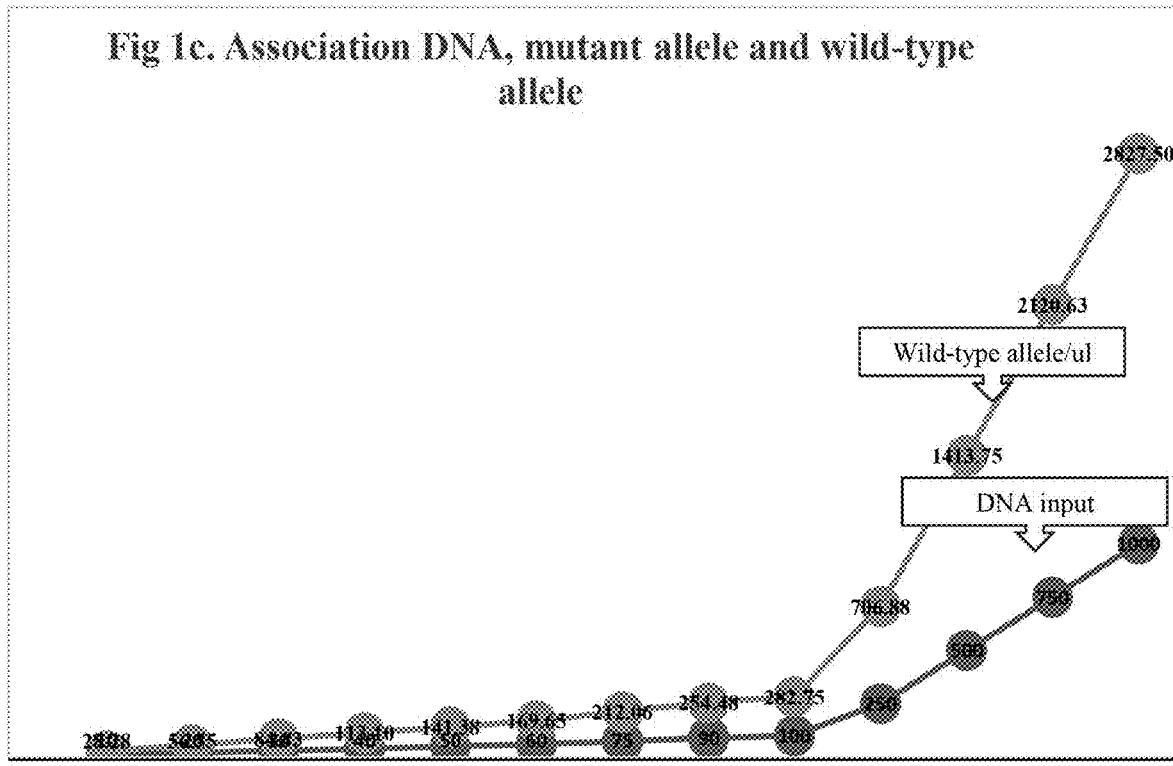

ALGORITHM TO EVALUATE EFFICACY OF DETECTING CELLULAR VARIANTS IN A HETEROGENEOUS CELL POPULATION

Multicellular organisms carry heterogenous cell populations, both in normal and disease conditions. Under disease conditions (e.g. Cancer), some cells undergo cellular and molecular changes that are associated with the incidence and/or progression of the disease; Identification of such changes helps in the diagnosis and adoption of treatment protocols (e.g. Somatic mutations are associated with cancer progression and treatment using targeted therapies). These changes are not inherited and could be present at low concentrations. Hence; there is a need for more sensitive assays to detect these changes in the background of heterogeneous cell populations. This in turn creates a need to evaluate the efficacy of detection of specific changes. A new algorithm, Detection Index. (DI), is proposed to evaluate the efficacy of detection. Detection Index is based on the combination of two basic factors, the number of copies of the target, and the ratio of target to that of wild-type in the sample.

REFERENCE CITED

U.S. Patent Documents

U.S. Pat. No. 9,920,366 Eltoukhy, et al. Mar. 20, 2018
U.S. Pat. No. 9,953,417 Byers, et al. Apr. 24, 2018
U.S. Pat. No. 9,953,209, Adalsteinsson, et al. Apr. 24, 2018

Other Publications

1. Geraats-Peters, C W M, Brouwers M-Steinberger, P M van der Zanden A G M, Bruisten S M, Weers-Pothoff G, Boel C H E, van den Brule A J C, Harmsen, H G and Hermans M H A. Specific and Sensitive Detection of Neisseria gonorrboeae in Clinical Specimens by Real-Time PCR. JOURNAL OF CLINICAL MICROBIOLOGY, November 2005, p. 5653-5659 Vol. 43, No. 11.
2. Schroth W., Haman U., Fasching P. A., Dauser S., et al. CYP2D6 polymorphisms as predictors of outcome in breast cancer patients treated with tamoxifen: expanded polymorphism coverage improves risk stratification. Clin Cancer Res. 2010; 16(17):4468-77.
3. https//www.nhlbi.nih.gov/health-topics/high-blood-pressure
4. https://www.cancer.gov/about-cancer/causes-prevention/risk.5. Shuhang Wang, Shundong Cang, and Delong Liu. Third-generation inhibitors targeting EGFR T790M mutation in advanced non-small cell lung cancer. J Hematol Oncol. 2016; 9: 34. Published online 2016 Apr. 12. doi; 10.1186/s13045-016-0268-z6. Grützmnann R, Molnar B, Pilarsky C, Habermann J K, Schlag P M, Saeger H D, Miehlke S, Stolz T, Model F, Roblick U J. Bruch H P, Koch R, Liebenberg V, Devos T, Song X, Day R H, Sledziewski A Z, Lofton-Day C (2008). "Sensitive detection of colorectal cancer in peripheral blood by septin 9 DNA methylation assay". PLoS ONE. 3 (11): e3759.
7. David A, Armbruster T P. Limit of Blank, Limit of Detection and Limit of Quantitation. Clin Biochem. Rev. 2008; 29: S49-52.
8. Detection of BRAF V600 Mutations in Metastatic Melanoma Comparison of the Cobas 4800 and Sanger Sequencing Assays. J. Mol. Diag. 2013; 15, November 15 790.795.
9. Pikor L A, Enfield K S, Cameron H, Lam W L. DNA extraction from paraffin embedded material for genetic and epigenetic analyses. J Vis Exp. 2011.
10. Weyant G W, Wisotzkey J D, Benko F A, Donaldson K J. BRAF mutation testing in solid tumors. A methodological comparison. J. Mol. Diag. 2014. Vol 16, No. 5
11. Vinayagamoorthy T, Zhang D, Ye F, Vinayagamoorthy D., Hodkinson R. Can detection of Braf p. V600E mutation be improved? Comparison of allele specific multiplex sequencing to present tests. Journal of Solid Tumors 2017; 7(2): 14-22.
12. https://www.accessdata.fda.gov/cdrh_docs/pdf12/P120014B.pdf
13. https://www.accessdata.fda.gov/cdrh_docs/pdf11/P110020B.pdf
14. Haber D A, Velculesc V E. Blood-Based Analyses of Cancer: Circulating Tumor Cells and Circulating Tumor DNA. Cancer Discov. 2014; 4(6):650-661.
15. Ellen H, Samantha P, Jochen B G, and Michael R. Speicher. The potential of liquid biopsies for the early detection of cancer. Precision Oncology (2017) 1:36.
16. M. W. Bessekri A. Aggoune S. Lazreg R. Bucht V. Fuller. Comparative study on the effects of reduced PCR reaction volumes and increased cycle number, on the sensitivity and the stochastic threshold of the AmpFISTR Identifiler Plus kit. Forensic Science International: Genetics Supplement. Series, Volume 4, Issue 1, 2013.
17. Richard Owczarzy, Bernardo G. Moreira, Yong You, Mark A. Behlke, and Joseph. A. Walder. Predicting Stability of DNA Duplexes in Solutions Containing Magnesium and Monovalent Cations. Biochemistry 2008, 47, 5336-5353
18. T. Hatada, K. Okada, H Ishii, et al. Evaluation of ultrasound-guided fine-needle aspiration biopsy for thyroid nodules Amu J Surg, 175 (1998), pp. 133-136.
19. Johnson G E. Mammalian cell HPRT gene mutation assay: test methods. *Methods Mol Biol.* 2012; 817:55-67. doi: 10.1007/978-1-61779-421-6 4.
20. Imperiale, T F, Ransohoff, D. F, Itzkowitz. S, H., Levin T R, Lavin, P, Lidgard, G P, Ahlquist, D A, Berger B M. Multitarget Stool DNA Testing for Colorectal-Cancer. Apr. 3, 2014. N. Engl J Med 2014; 370:1287-1297 DOT: 10.1056.
21. Dahmcke C M, Steven K E, Larsen L K, Poulsen A L. Abdul-Al A, Dahl C, Guldberg P. A Prospective Blinded Evaluation of Urine-DNA Testing for Detection of Urothelial Bladder Carcinoma in Patients with Gross Hematuria. *Eur UroL* 2016 December; 70(6): 916-919. doi: 10.1016/j.eururo.2016.06.035. Epub 2016 Jul. 11.
22. Cohen N, Gupta M, Doerwald-Munoz L, Jan D, Young J E, Archibald S, Jackson B, Lee J, Chernesky M. Developing a new diagnostic algorithm for human papilloma virus associated oropharyngeal carcinoma: an investigation of HPV DNA assays. *J Otolaryngol Head Neck Surg.* 2017 Feb. 13; 46(1):11. doi: 10.1186/s40463-017-0189.
23. Huang T Y, Piunti A, Lulla R R, Qj J, Horbinski C M, Tomita T, James C D, Shilatifard A, Saratsis A M. Detection. of Histone H3 mutations in cerebrospinal fluid-derived tumor DNA from children with diffuse midline glioma Acta Neuropathol Commun. 2017 Apr. 17; 5(1):28. doi: 10.1186/s40478-0170436-6.
24. Park S, Hur J Y, Lee K Y, Lee J C, Rho J K, Shin S H, Choi C M. Assessment of EGFR mutation status using cell-free DNA from bronchoalveolar lavage fluid. Clin Chem Lab Med. 2017 Aug. 28; 55(10):1489-1495. doi: 10.1515/cclm-2016-0302.
25. Zuo Y, Lv Y, Qian X, Wang S, Chen Z, Jiang Q, Cao C, Song Y. Inhibition of HHIP Promoter Methylation Suppresses Human Gastric Cancer Cell Proliferation and Migration Cell Physiol Biochem. 2018; 45(5): 1840-1850. doi: 10.1159/000487875. Epub. 2018 Feb. 28.
25. Maemondo M. et al. Gefitinib or chemotherapy for non-small-cell lung cancer with mutated EGFR. N Engl. J Med 362, 2380-2388 (2010).
26. Verghese P S, Schmeling D O, Filtz E A, Grimm J M, Matas A J, Balfour. H H Jr. Transplantation of solid organ recipients shedding Epstein-Barr virus DNA pre-transplant: A prospective study. Clin Transplant 2017 November; 31(11). doi: 10.11.11/ctr:13116. Epub 2017 Oct. 8.
27. Cibulskis, K, Lawrence M S, Carter S L, Sivachenko A, Jaffe D, et al. (2013) Sensitive detection of somatic point mutations in impure and heterogeneous cancer samples. Nature Biotechnology 31: 213-219.
28. Pan Q, Shai O, Lee L J, Frey B J, Blencowe, B J. Deep surveying of alternative splicing complexity in the human transcriptome by high-throughput sequencing *Nat Genet* 2008; 40: 1413-1415.
29. Anders H. Lund Maarten van Lohuizen Epigenetics and cancer. Gene Development. 2004. 18: 2315-2335.
30. Smadbeck J B; Johnson S H, Smoley S A, Gaitatzes A, Drucker T M, Zenka R M, Kosari F, Murphy S J, Hoppman N, Aypar U, Sukov W R, Jenkins R B, Kearney H M, Feldman A L, Vasmatzis G. Copy Number Variant Analysis using Genome-Wide Mate-Pair Sequencing. Genes Chromosomes Cancer. 2018 May 4. doi: 10.1002/gcc.5.
31. Todd C. Lorenz Polymerase Chain Reaction: Basic Protocol Plus Troubleshooting and Optimization Strategies. J Vis Exp. 2012; (63): 3998. Published online 2012 May 22. doi: 10.3791/3998
32. Bollag G, Tsai J, Zhang J, Zhang C, Ibrahim P, Nolop K, Hirth P (November 2012). "Vemurafenib: the first drug approved for BRAF-mutant cancer". Nat Rev Drug Discov. 11 (11): 873-86. doi:10.1038/nrd3847 PMID 23060265.
33. Nie K, Jiang H, Zbang C, Geng C, Xu, X, Zhang L, Zhang H, Zhang Z, Lan K, Ji Y Mutational Profiling of Non-Small-Cell Lung Cancer Resistant to Osimertinib Using Next-Generation Sequencing in Chinese Patients. Biomed Res lit. 2018 Mar. 11; 2018:9010353. doi: 10.1155/2018/9010353. eCollection 2018.
34. Buckley B, Pierce B. Targeted inhibition of the BRAF pathway in a patient with stage IV melanoma, JAAPA. 2018 May; 31(5):24-26. doi: 10.1097/01. JAA.0000530293.13871.69
35. Kim D M, Kim D H, Jung W, Lee K Y, Kim D E. Fluorometric detection of EGFR exon 19 deletion mutations in lung cancer cells using graphene oxide. Analyst. 2018 Apr. 16; 143(8):1797-1804. doi: 10.1039/C8AN00098K.
36. Warren J D, Xiong W, Bunker A M, Vaughn C P, Furtado L V, Roberts W L, Fang J C, Samowitz W S, Heichmnan K A. Septin 9 methylated DNA is a sensitive and specific blood test for colorectal cancer. BMC Med. 2011 Dec. 14; 9:133. doi: 10.1186/1741-7015-9-133.

BACKGROUND OF INVENTION 1. Field of Invention

This invention relates to evaluating the efficacy of detecting molecular and cellular changes in a heterogeneous cell population. The invention proposes an algorithm (Detection index), which is a combination of two basic, determinants; the lower limit of detection of the target, and the ratio of target to that of wild-type.

2. Prior Art

The invention is applicable to all molecular and cellular changes that differ from the status quo, what is referred to as wild type, and the invention is best explained using detection of somatic mutations for the use of targeted chemotherapy. Laboratory investigation commonly uses two parameters, sensitivity and specificity, to evaluate the efficacy of detection of a disease-specific analyte. Such evaluation depends on the output signal of the device used. This in turn leads to the signal output being correlated with the analyte (target) causing the disease (e.g. detection of gonorrhea), a disease condition (e.g. increased blood glucose), a predisposition to disease (e.g. increased blood pressure) or a treatment outcome (e.g. genetic variant of Cyp 2D6) using appropriate analytical devices (1, 2, 3), Progression of cancer is a multi-factorial event, of which somatic mutations are one group of determinants and not the only deciding factors for the progression of the disease (4). Traditionally, cancer is diagnosed using histochemical methods, where the presence of transformed cells confirms cancer. Further, some of these transformed cells could harbor specific changes (e.g. genetic/epigenetic) known as somatic mutations (5,6). Although some of these somatic mutations are associated with disease progression, they are only part of the determinant of the disease progression and not the sole factor. However, somatic mutations are detected for very specific purposes. For example, Brafp.V600E/K mutation is detected for treating late stage melanoma with Zelboraf. Although there is validity in correlating transformed cells with progression of the disease, there is no validity in evaluating the efficacy of detection of somatic mutations to clinical outcome, hence the present version of specificity and sensitivity is not scientifically valid. Further, there are no gold standard assays for detection of somatic mutations. Therefore, there is a need to define a new parameter based on factors that determine the ability to detect such somatic mutations in a heterogenous cell population.

Laboratory investigations are performed to detect specific analyte(s) that could differentiate the patient population from normal population and/or to monitor treatment modalities. In doing so, efficacy of detection of the intended analyte is determined by the ability of the assay to detect a minimum amount of the analyte in a patient sample, referred to as the lower limit of detection (7). Companion diagnosis is a standard procedure in the management of cancer, and determination of somatic mutations for targeted chemotherapy is one such component of laboratory investigation (8), Tumor content of a biopsy is defined as the ratio of the cancer cells to that of the normal cells and is widely used as an indicator of efficacy of the companion diagnostic for two practical reasons; (a) the histological analysis of a tumor biopsy is a standard procedure, and tumor content is part of the results of the routine histological analysis, (b) the DNA for the detection of any genetic variants is extracted from the same histological slides (9). Naturally, tumor content became a choice of convenience to grade the efficacy, of detection, often presently referred to as 'sensitivity'. Hence, sensitivity is defined as the ratio of cancer cells to normal cells in a heterogeneous cell population. Further, different companion, diagnostic platforms, including Sanger sequencing, have their own analytical validation, with specific cut offs of tumor content and DNA input for their respective analysis (10-15). Molecular methods use primers for amplification and probes for identification, where target specific primers and probes are supposed to bind to their respective templates. However, such binding is also affected by ionic concentrations, temperature etc. (16,17). Hence, as an exception to the rule, there is a possibility of cross binding where the primers specific to the mutated template binds to the wild-type template and vice versa. Therefore, the efficacy of detection of the target depends on the relative competitiveness of the target and wild-type target templates to their respective primers/probes. Tumor content is a measure of the relative amount of the transformed cells to that of the non-transformed cells, hence it is a false measure of the competitiveness of mutant and wild-type probes and/or primers to either of the templates in a heterogeneous cell population. Hence, the true measure of the competitiveness will be the ratio of the number of copies of mutant allele to that of wild type in the sample that competes for its specific primers and/or probes.

SUMMARY OF THE INVENTION

There is a clinical need to detect specific targets in a heterogenous population that could have both diagnostic and therapeutic value. The present evaluation parameters such as specificity and sensitivity are not scientifically valid for reasons mentioned in prior art. Further, tumor content does not reflect the molecular competitiveness, as mentioned in the previous section. Hence, there is a need for a new way to evaluate the efficacy of detection that is based on true determinants.

Detection of the specific somatic mutation imposes two challenges; (a) the detection of the mutant allele at a minimum number of copies as possible, which is defined as the Lower Limit of Detection, and (b) the detection of somatic mutations in a heterogenous cell population carrying wild-type in formalin fixed paraffin embedded tissue. This invention is based on two basic factors; the lower limit of detection the second parameter is the ratio of the target mutation allele to that of the wild type allele in the sample. In doing so, the tumor content in the sample is used as the initial entry point where the mutant allele and the wild type allele is calculated. Both the lower limit of detection and the amount of mutant allele and the total wild type alleles are inversely proportionate the efficacy of detection. Hence, these factors are integrated to formulate a new parameter of evaluation, Detection Index.

Sample size is one key factor in clinical diagnosis. The importance of sample size becomes very evident in fine needle biopsy (18). Although lower limit of detection is a determinant factor, present evaluation of companion diagnosis methods totally depends on tumor content, (E.g. Formalin Fixed Paraffin Embedded tissue). Further, determining tumor content is not practical in analyzing liquid biopsy samples, and hence will solely depend on the lower limit of detection. Hence, there is a need for new evaluation criteria that can be applied to all relevant clinical samples. Other aspects of the invention are described below.

1. An algorithm. Compared to infectious diseases and pharmacogenetics, testing for somatic mutations brings in additional technical challenges as stated above. Further, the absence of any acceptable reference methods to evaluate the efficacy of testing, an algorithm is formulated as Detection index. The DI is based on two basic factors; (a) the number of copies of the mutant allele, and (b) the ratio of the copies of mutant allele to that of the wild-type allele.
2. Reporting and clinical utilities. Just like in clinical chemistry (e.g. determination of blood sugar), use of Detection index will enable companion diagnosis to define its limit of efficacy using two: data points. Operating within such a limit will eliminate potential false negatives or false positives of the test. Since Detection index is a true scientific evaluation of the tests, clinical data interpretation and improved treatment strategies could be adopted.

$$\text{Amount of } DNA = \frac{\text{Copies of Mutant Allele} \times 100}{290\% \text{ tumor contents}}.$$

3. The heterogeneous cell sample type includes solid tumors, liquid biopsy, mammalian cell culture, stool, urine, saliva, cerebrospinal fluids, lung lavage, gastric, and tissue and/or organ transplants (19,20,21,22,23,24, 25,26,27). Further, the genetic variants could be single nucleotide polymorphism, more than one mutation, deletion, additions of nucleotides, epigenetic changes (e.g. Methylation); gene expression, splice variants and copy number variations of all the above genetic variants (28,29,30).
4. As described earlier, the DNA input and tumor content are interchangeable. That means that in the case of a sample that has low tumor content, the end user could use the recommended amount of DNA and vice versa. Thus, the end user has the freedom over the design of the assay. For example, once the desired Detection index is decided, one could determine the amount of DNA input based on the tumor content.
5. Patient care. The present use of 'sensitivity' for evaluation is a measure of convenience that falls short of scientific accuracy. Since the choice of targeted chemotherapy and its use depends on the detection of specific somatic mutations, the selection of companion diagnosis becomes very critical, carrying the burden of accuracy for: patients fighting for recovery.
6. Regulatory. Use of MI will also help regulatory institutions, such as the FDA, to evaluate clinical tests more objectively, reflecting a true measure of efficacy.

DETAILED DESCRIPTION OF THE INVENTION

It is summarized that two basic factors that determine the efficacy of detection of the mutant allele are the;
(a) Number of copies of mutant alleles in the reaction. The assay that detects with lesser number of copies of mutant allele, the more efficient the assay.
(b) Number of wild-type alleles in the reaction. The assay that detects the mutant, allele in the presence of higher copies of wild-allele, the more efficient the assay.

Polymerase chain reaction (PCR) is an integral part of companion diagnosis and is performed in an optimum reaction volume to avoid nonspecific amplification, while at the same time to be effective in amplifying the intended: target DNA. However, for practical reasons, present companion diagnosis is performed in small volumes (5 ul-20 ul), which could compromise the overall assay (31). Since reaction volume is variable, for evaluation purposes, it is more appropriate have (a) and (b) per ul:

Now that the two determinants, have been characterized, one could combine them into an algorithm, Detection index. Since a fewer number of copies of the mutant allele is necessary for detection, the more efficient the assay, hence the efficacy, of detection is inversely proportional to the number of copies of mutant allele/ul. Further, the assay is more efficient if the ratio of mutant: wild-type is higher; hence DI is inversely proportional.

On this basis, a DI algorithm, is derived as follows:

$$DI = /MC \times 1/\text{Ratio of } WC:MC$$

Where MC is copies of mutant allele/ul and WC is copies of wild-type allele/ul

Calculation of DI requires only two data points, the tumor content and the amount of DNA used. Both the number of copies of the mutant allele/ul and wild-type allele/ul can be calculated using:

$$\text{Copies of Mutant Allele} = \frac{\text{Amount of } DNA \times 290 \times 100\% \text{ tumor content}}{100}$$

Note: 1 ng of human. DNA contains 290 haploid copies

Similarly, the number of copies of wild type allele is determined as;

$$\text{Wild-type content} = \frac{(\text{Amount } DNA \times \% \text{ tumor content}) + (\text{Amount } DNA \times 290 \times 100 - \text{Tumor content}) \times 2}{100}$$

The invention is illustrated in detail with the following scenarios.

a. As shown in Table 1, the tumor content is not the same as the ratio of mutant allele to that of the wild-type. Although with a fixed amount of DNA. (e.g. 40 ng) input there is a proportional correlation of tumor content and the number of copies of mutant allele, both depart disproportionately at higher tumor content (FIG. 1a). A similar-pattern is found when tumor content is compared to the ratio of the mutant to wild-type alleles (FIG. 1b).

Detection of somatic mutation is not a standardized procedure; hence there are variations in all key steps including DNA extraction (Sample preparation). These variations include using varying numbers (2-10) of FFPE sections per assay, and varying thickness (5 mm-10 mm) of the FFPE sections, thus resulting in varying amounts of DNA input per reaction. Table 2 shows that although tumor content is 5%, the allele ratio (Mutant: Wild) is 2.5. Secondly, with the increasing amount of DNA per assay, the association between DNA input and ratio of the wild-type allele is disproportionate (FIG. 1c).

b. Another illustration shows that with fixed. DNA input per assay (40 ng) and with varying tumor content, the number of copies of mutant allele/ul varies from 5.8 copies/ul to 580 copies/ul (Table 1), On the other hand, with fixed tumor content (5%) per assay and varying amount of DNA input, the number of copies of mutant allele/ul varies from 7.3 copies/ul to 725 copies/ul (Table. 2). Hence, an assay capable of detecting positives (29 copies of mutant allele/ul) with 40 ng of DNA at 5% tumor content will report a sample that carries. 50 mutant copies/ul as positive, whereas the assay that is capable of detecting (348 copies/ul) with 40 ng of DNA at 60% tumor content will report as negative. Similarly, an assay capable of detecting somatic mutations in 5% tumor content with 50 ng of DNA could only detect in a sample that has more than 36.3 mutant allele/ul. Therefore, this same assay would report a sample with 5% tumor content using 10 ng of DNA as negative. Hence, having tumor content as a measure of accuracy could lead to false negatives resulting in preventing patients from receiving beneficial targeted chemotherapy. These examples show that there are discrepancies among methods determining the efficacy of detection based on the tumor content or the amount of DNA input alone.

c. In another illustration, Table 2, shows two sets of DIs; one with 40 ng of DNA input (Table 1) with varying tumor content where the Detection index decreases with increase in tumor content, and other varying DNA input at 5% tumor content (Table 2) where the DI decreases with an increase in DNA input. With this interactive table for a desired detection index, one could determine either the amount of DNA needed if tumor content is known or vice versa.

EXAMPLES

Example 1

Nucleic acid based. Genetic changes are a common occurrence in human and other life forms. Some of these genetic changes occur as somatic mutations that are associated with disease state such as cancer. Hence there is a need to detect these somatic mutations from clinical samples such as solid tumors, liquid biopsy; urine and other body: fluids. Further, these changes could be genetic changes that include single point mutations, deletion, additions, gene expression, splice variants/isomers epigenetic changes such as methylation. In the recent past there have been a number of drugs developed to act on those specific somatic mutations (32,33). Further, some of these genetic and epigenetic changes are associated with progression of the disease. Hence, detection of these specific genetic and epigenetic changes is vital for diagnostic, treatment and prognostic purposes. Some of the targets are listed below.

a. Braf p. V600E/K for treatment of metastatic melanoma (34)

b. Deletion A747-750: in epidermal growth factor receptor (EGFR) is associated with incidence and progression of non-small cell lung-cancer (35).

c. Methylation in the CpG region of the gene acts as the on/off switch which controls expression of the gene. There are number of isoforms produced by SEPT gene that is associated with colorectal cancer (36).

d. Androgen receptor. There are more than 20,000 functional genes in human and many of them undergo post transcriptional editing (splicing) producing number of variant mRNA template that are translated into corresponding protein isomers. A Splice variant (ARV7) is associated with the treatment resistant prostate cancer.

Example 2

Protein based. Another illustration of this invention is in the detection of protein isoforms. The isomers are also formed based on post translational modification (E.g. glycoforms). These protein isoforms can be detected either by liquid chromatography, mass spectrometry, or by detecting specific rRNA, and predicting the protein structure by computational modelling. Further, proteins isoforms can be further characterized by their respective epitopes or their building subunits including, loops, beta sheet and helical coil.

Example 3

Cell based. Another illustration of this invention is detection of stem cells. Adult stein cells are a small number of undifferentiated cells found in various tissues that function as a battery of cells that could divide and replenish adult tissues when needed. These cells are also being studied as a potential source of cancer. There is also need to detect embryonic stem cells that are used in tissue organ development.

BRIEF DESCRIPTION OF THE TABLES AND FIGS

Table 1. This table calculates mutant allele/ul, wild type allele per ul, allele ratio, with fixed DNA input (40 ng) and varying tumor content generating corresponding Detection Index.

Table 2. This table calculates mutant allele/ul, wild type allele per ul, allele ratio, with fixed tumor content (5%) and varying DNA input generating corresponding detection Index.

FIG. 1a. Shows the correlation of mutant allele/ul with increasing tumor content at fixed DNA input (40 ng).

FIG. 1b. Shows the correlation of allele ratio with increasing tumor content at fixed DNA input (40 ng).

FIG. 1c. Shows the correlation of mutant alleles per ul and wild type allele with increasing DNA input.

TABLE 1a

Varying tumor content with 40 ng of DNA

| % Tumor content | Mutant allele/ul | Wild type allele/ul | % Allele Ratio (M:W) | DI |
|---|---|---|---|---|
| 1 | 5.8 | 1154 | 0.5 | 3448.28 |
| 2 | 11.6 | 1148 | 1.0 | 862.07 |
| 5 | 29.0 | 1131 | 2.5 | 137.93 |
| 10 | 58.0 | 1102 | 5.0 | 34.48 |
| 20 | 116.0 | 1044 | 10.0 | 8.62 |
| 30 | 174.0 | 986 | 15.0 | 3.83 |
| 40 | 232.0 | 928 | 20.0 | 2.16 |
| 50 | 290.0 | 870 | 25.0 | 1.38 |
| 60 | 348.0 | 812 | 30.0 | 0.96 |
| 70 | 406.0 | 754 | 35.0 | 0.70 |
| 80 | 464.0 | 696 | 40.0 | 0.54 |
| 90 | 522.0 | 638 | 45.0 | 0.43 |
| 100 | 580.0 | 580 | 50.0 | 0.34 |

TABLE 1b

Varying DNA with 5% tumor content

| DNA input | Mutant allele/ul | Wild allele/ul | % Allele Ratio (M:W) | DI |
|---|---|---|---|---|
| 10 | 7 | 282.75 | 2.5 | 551.724 |
| 20 | 15 | 565.50 | 2.5 | 275.862 |
| 30 | 22 | 848.25 | 2.5 | 183.908 |
| 40 | 29 | 1131.00 | 2.5 | 137.931 |
| 50 | 36 | 1413.75 | 2.5 | 110.345 |
| 60 | 44 | 1696.50 | 2.5 | 91.954 |
| 75 | 54 | 2120.63 | 2.5 | 73.563 |
| 90 | 65 | 2544.75 | 2.5 | 61.303 |
| 100 | 73 | 2827.50 | 2.5 | 55.172 |
| 250 | 181 | 7068.75 | 2.5 | 22.069 |
| 500 | 363 | 14137.50 | 2.5 | 11.034 |
| 750 | 544 | 21206.25 | 2.5 | 7.356 |
| 1000 | 725 | 28275.00 | 2.5 | 5.517 |

What I claim is:

1. A method of comparing detection indices of two or more tests performed separately, each test comprises;
 (b) using a clinical specimen carrying cancer cells with heterozygous alleles for a somatic mutation, and
 (c) viewing in a microscopic field counting total number of cells and the total number of cancer cells, and dividing the total number of cancer cells by the total number of cells, generating the tumor content, and multiplying the tumor content by 100 to determine the percentage tumor content, and
 (d) extracting the total DNA from the clinical sample, and using spectrophotometer to determine the DNA concentration (ng/ul) of the DNA extract, and multiplying volume (ul) of DNA extract added to the reaction by the DNA concentration to determine the amount of DNA, and
 (e) adding up the volumes of reagents added to the reaction to determine the reaction volume (ul), and
 (e) calculating the number of copies of the mutant allele (MC) per milliliter by $$\frac{\text{Amount of } DNA \times 290 \times \% \text{ tumor content}}{\text{Reaction volume } (\mu l) \times 100}$$

(f) calculating number of copies of wild type allele (WC) per milliliter by $$\frac{(\text{Amount of } DNA \times 290 \times \% \text{ tumor content}) + [(\text{Amount of } DNA \times 290 \times 100 - \% \text{ Tumor content}) \times 2]}{\text{Reaction volume}(\mu l) \times 100}$$

and
 (g) determining the detection index by multiplying the inverse of (MC) and inverse of the ratio of (MC:WC), and
 the test with higher detection index is more sensitive in detecting the somatic mutation.

2. A method of claim 1, wherein the somatic mutant is Braf p.V600E.

3. A method of claim 1, wherein the somatic mutant is EGFR L858R.

4. A method of claim 1, wherein the somatic mutant is EGFR T790M.

5. A method of claim 1, wherein the somatic mutant is EGFR del A747_750.

6. A method of claim 1, wherein the somatic mutant is Kras G12D.

7. A method of claim 1, wherein the somatic mutant is Kras G12V.

8. A method of claim 1, wherein the somatic mutant is Kras G12C.

9. A method of claim 1, wherein the somatic mutant is Kras G13D.

10. A method of claim , wherein the somatic mutant is PIK3CA.

11. A method of claim 1, wherein the clinical sample is tissue biopsy.

12. A method of claim 1, wherein the clinical sample is liquid biopsy.

13. A method of claim 1, wherein the clinical sample is sputum.

14. A method of claim 1, wherein the clinical sample is stool.

15. A method of claim 1, wherein the clinical sample with stem cells.

* * * * *